(12) United States Patent
McKiernan et al.

(10) Patent No.: US 8,916,677 B2
(45) Date of Patent: Dec. 23, 2014

(54) MONOMER, POLYMERIZATION METHOD, AND POLYMER

(75) Inventors: Mary McKiernan, Cottenham (GB); Thomas Pounds, Cambridge (GB)

(73) Assignees: Cambridge Display Technology Limited, Cambridgeshire (GB); Sumitomo Chemical Company Limited, Tokyo (JP)

( * ) Notice: Subject to any disclaimer, the term of this patent is extended or adjusted under 35 U.S.C. 154(b) by 364 days.

(21) Appl. No.: 13/258,910

(22) PCT Filed: Apr. 15, 2010

(86) PCT No.: PCT/GB2010/000801
§ 371 (c)(1),
(2), (4) Date: Oct. 31, 2011

(87) PCT Pub. No.: WO2010/119275
PCT Pub. Date: Oct. 21, 2010

(65) Prior Publication Data
US 2012/0053315 A1    Mar. 1, 2012

(30) Foreign Application Priority Data
Apr. 16, 2009   (GB) .................................. 0906553.3

(51) Int. Cl.
| | | |
|---|---|---|
| C08G 59/24 | (2006.01) | |
| C08G 61/12 | (2006.01) | |
| C07D 265/38 | (2006.01) | |
| H01L 51/00 | (2006.01) | |
| C09K 11/06 | (2006.01) | |
| C08G 59/00 | (2006.01) | |
| H01L 51/50 | (2006.01) | |

(52) U.S. Cl.
CPC ........ *C08G 61/122* (2013.01); *C08G 2261/364* (2013.01); *C09K 2211/1475* (2013.01); *C08G 2261/3245* (2013.01); *C07D 265/38* (2013.01); *H01L 51/5012* (2013.01); *H01L 51/0035* (2013.01); *C08G 2261/5222* (2013.01); *C09K 2211/1466* (2013.01); *C09K 11/06* (2013.01); *C08G 2261/3162* (2013.01); *C09K 2211/1483* (2013.01); *C08G 61/12* (2013.01)
USPC ........... 528/403; 528/394; 528/397; 528/423; 528/424

(58) Field of Classification Search
USPC ........................... 528/403, 423, 424, 394, 397
See application file for complete search history.

(56) References Cited

U.S. PATENT DOCUMENTS

| 4,539,507 A | 9/1985 | VanSlyke et al. |
| 5,150,006 A | 9/1992 | Van Slyke et al. |

(Continued)

FOREIGN PATENT DOCUMENTS

| EP | 0 612 826 A1 | 8/1994 |
| EP | 0 707 020 A2 | 4/1996 |

(Continued)

OTHER PUBLICATIONS

Bernius et al., "Progress with Light-Emitting Polymers," *Adv. Mat.*, 12(23):1737-1750 (2000).

(Continued)

*Primary Examiner* — Duc Truong
(74) *Attorney, Agent, or Firm* — Marshall, Gerstein & Borun LLP

(57) ABSTRACT

A monomer of formula (III):

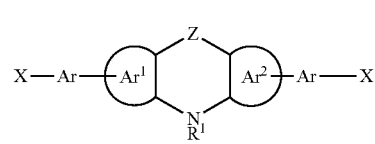

(III)

wherein X is a polymerisable group Ar, $Ar^1$ and $Ar^2$ each independently represent an optionally substituted aryl or heteroaryl group; $R^1$ represents H or a substituent; and Z represents a direct bond or a divalent linking atom or group, wherein $Ar^1$ and $Ar^2$ are linked by a single bond or a divalent linking group selected from $CR^1R^2$, $SiR^1R^2$, $PR^1$, $NR^1$, O and S wherein $R^1$ and $R^2$ are independently selected from hydrogen; optionally substituted alkyl wherein one or more non-adjacent C atoms may be replaced with O, S, N, C=O and —COO—; alkoxy, aryl, arylalkyl, heteroaryl and heteroarylalkyl. $Ar^1$ and $Ar^2$ are preferably linked by an oxygen atom, and $Ar^1$ and/or $Ar^2$ may be fused to their respective adjacent Ar groups. $Ar^1$ and its adjacent Ar group and/or $Ar^2$ and its adjacent Ar group are optionally fused to form a fluorene unit.

12 Claims, 3 Drawing Sheets

(56) References Cited

U.S. PATENT DOCUMENTS

| | | |
|---|---|---|
| 5,432,014 A | 7/1995 | Sano et al. |
| 5,621,131 A | 4/1997 | Kreuder et al. |
| 5,723,873 A | 3/1998 | Yang |
| 5,798,170 A | 8/1998 | Zhang et al. |
| 6,083,634 A | 7/2000 | Shi |
| 6,268,695 B1 | 7/2001 | Affinito |
| 6,353,083 B1 | 3/2002 | Inbasekaran et al. |
| 7,094,477 B2 | 8/2006 | Kamatani et al. |
| 7,125,998 B2 | 10/2006 | Stossel et al. |
| 7,147,935 B2 | 12/2006 | Kamatani et al. |
| 7,238,435 B2 | 7/2007 | Kamatani et al. |
| 7,348,428 B2 | 3/2008 | O'Dell et al. |
| 2002/0117662 A1 | 8/2002 | Nii |
| 2002/0182441 A1 | 12/2002 | Lamansky et al. |
| 2005/0256290 A1 | 11/2005 | Cella et al. |
| 2006/0166038 A1 | 7/2006 | Park et al. |
| 2008/0122346 A1 | 5/2008 | Lyu et al. |
| 2011/0186826 A1 | 8/2011 | Steudel et al. |

FOREIGN PATENT DOCUMENTS

| | | |
|---|---|---|
| EP | 0 842 208 A1 | 5/1998 |
| EP | 0 880 303 A1 | 11/1998 |
| EP | 0 901 176 A2 | 3/1999 |
| EP | 0 947 123 A1 | 10/1999 |
| EP | 0 949 850 A1 | 10/1999 |
| EP | 1 245 659 A1 | 10/2002 |
| EP | 2 048 176 A1 | 4/2009 |
| GB | 2 348 316 A | 9/2000 |
| JP | 2002-324679 A | 11/2002 |
| JP | 2003-165829 A | 6/2003 |
| JP | 2005-054165 A | 3/2005 |
| JP | 2005-506419 A | 3/2005 |
| JP | 2008-280386 A | 11/2008 |
| JP | 2011-529110 A | 12/2011 |
| WO | WO-90/13148 A1 | 11/1990 |
| WO | WO-98/10621 A1 | 3/1998 |
| WO | WO-98/57381 A1 | 12/1998 |
| WO | WO-99/48160 A1 | 9/1999 |
| WO | WO-99/54385 A1 | 10/1999 |
| WO | WO-00/48258 A1 | 8/2000 |
| WO | WO-00/53656 A1 | 9/2000 |
| WO | WO-00/55927 A1 | 9/2000 |
| WO | WO-01/19142 A1 | 3/2001 |
| WO | WO-01/62869 A1 | 8/2001 |
| WO | WO-01/81649 A1 | 11/2001 |
| WO | WO-02/31896 A2 | 4/2002 |
| WO | WO-02/44189 A1 | 6/2002 |
| WO | WO-02/45466 A1 | 6/2002 |
| WO | WO-02/066552 A1 | 8/2002 |
| WO | WO-02/068435 A1 | 9/2002 |
| WO | WO-02/081448 A1 | 10/2002 |
| WO | WO-02/084759 A1 | 10/2002 |
| WO | WO-03/018653 A1 | 3/2003 |
| WO | WO-03/022908 A1 | 3/2003 |
| WO | WO-03/095586 A1 | 11/2003 |
| WO | WO-2006/096399 A2 | 9/2006 |
| WO | WO-2010/010356 A2 | 1/2010 |

OTHER PUBLICATIONS

Ku et al., "PLED Device Containing Triphenyamine-Derived Polyurethanes as Hole-Transporting Layers Exhibit High Current Efficiencies," *J. Mater. Chem.*, 18:1296-1301 (2008).

Kulkarni et al., "New Ambipolar Organic Semiconductors. 2. Effects of Electron Acceptor Strength on Intramolecular Charge Transfer Photophysics, Highly Efficient Electroluminescence, and Field-Effect Charge Transport of Phenoxazine-Based Donor-Acceptor Materials," *Chem. Mater.*, 20:4212-4223 (2008).

Kulkarni et al., "Photodegradation of Emissive Conjugated Copolymers and Oligomers Containing Thienopyrazine," *Macromolecules*, 41(2):339-345 (2007).

Michaelson, "The work function of the elements and its periodicity", *J. Applied Physics*, 48(11): 4729-4733 (1977).

Niu et al., "Thermal Annealing Below the Glass Transition Temperature: A General Way to Increase Performance of Light-Emitting Diodes Based on Copolyfluorenes," *Appl. Phys. Lett.*, 81(4):634-636 (2002).

Setayesh et al., "Bridging the Gap Between Polyfluorene and Ladder-Poly-p-phenylene: Synthesis and Characterization of Poly-2,8-indenofluorene," *Macromolecules*, 33(6):2016-2020 (2000).

Tokito et al., "Metal oxides as a hole-injecting layer for an organic electroluminescent device", *J. Phys. D: Appl. Phys.*, 29:2750-2753 (1996).

Yamaguchi et al., "Effects of B and C on the Ordering of $L1_0$-CoPt Thin Films," *Appl. Phys. Lett.*, 79(5):2001-2003 (2001).

Yamamoto, "Electrically Conducting and Thermally Stable π-Conjugated Poly(Arylenes)s Prepared by Organometallic Processes," *Prog. Polym. Sci.*, 17:1153-1205 (1993).

Yang et al., "Efficient blue polymer light-emitting diodes from a series of soluble poly(paraphenylene)s", *J. Appl. Phys.*, 79(2):934-939 (1996).

Combined Search and Examination Report for Application No. GB0906553.3, dated Dec. 10, 2009.

Examination Report for Application No. GB0906553.3, dated Jun. 15, 2011.

International Search Report and Written Opinion for Application No. PCT/GB2010/000801, dated Jul. 30, 2010.

International Preliminary Report on Patentability for Application No. PCT/GB2010/000801, dated Oct. 18, 2011.

Partial English translation of Office Action for corresponding Japanese Patent Application No. 2012-0505234, dated Oct. 1, 2013.

MONOMER, POLYMERIZATION METHOD, AND POLYMER

This application is a 371 of PCT/GB2010/000801 filed on Apr. 15, 2010.

FIELD OF THE INVENTION

This invention relates to monomers and a method of forming polymers for organic electronic devices, in particular charge transporting and light-emitting polymers for organic electroluminescent devices.

BACKGROUND OF THE INVENTION

One class of opto-electrical devices is that using an organic material for light emission or detection. The basic structure of these devices is a light emissive organic layer, for instance a film of a poly (p-phenylenevinylene) ("PPV") or polyfluorene, sandwiched between a cathode for injecting negative charge carriers (electrons) and an anode for injecting positive charge carriers (holes) into the organic layer. The electrons and holes combine in the organic layer generating photons. In WO90/13148 the organic light- emissive material is a conjugated polymer. In U.S. Pat. No. 4,539,507 the organic light-emissive material is of the class known as small molecule materials, such as (8-hydroxyquinoline) aluminum ("Alq3"). In a practical device one of the electrodes is transparent, to allow the photons to escape the device.

A typical organic light-emissive device ("OLED") is fabricated on a glass or plastic substrate coated with a transparent anode such as indium-tin-oxide ("ITO"). A layer of a thin film of at least one electroluminescent organic material covers the first electrode. Finally, a cathode covers the layer of electroluminescent organic material. The cathode is typically a metal or alloy and may comprise a single layer, such as aluminum, or a plurality of layers such as calcium and aluminum. In operation, holes are injected into the device through the anode and electrons are injected into the device through the cathode. The holes and electrons combine in the organic electroluminescent layer to form an exciton which then undergoes radiative decay to give light.

These devices have great potential for display and lighting applications. However, there are several significant problems. One is to make the device efficient, particularly as measured by its external power efficiency and its external quantum efficiency. Another is to reduce the voltage at which peak efficiency is obtained. Another is to stabilize the voltage characteristics of the device over time. Another is to increase the lifetime of the device.

Conjugated polymers may be formed by a metal-catalyzed polymerization reaction which operate via a "metal insertion" wherein the metal atom of a metal complex catalyst is inserted between an aryl group and a leaving group of a monomer. By this process, aromatic monomers comprising two or more reactive leaving groups can be polymerized to form chains of aromatic repeat units. Examples of such polymerization techniques are Suzuki polymerization as described in, for example, WO 00/53656 and Yamamoto polymerization as described in, for example, T. Yamamoto, "Electrically Conducting And Thermally Stable pi -Conjugated Poly(arylene)s Prepared by Organometallic Processes", Progress in Polymer Science 1993, 17, 1153-1205. In the case of Yamamoto polymerization, a nickel complex catalyst is used; in the case of Suzuki polymerization, a palladium complex catalyst is used.

For example, in the synthesis of a linear polymer by Yamamoto polymerization, a monomer having two reactive halogen groups is used. Similarly, according to the method of Suzuki polymerization, at least one reactive group is a boron derivative group such as a boronic acid or boronic ester and the other reactive group is a halogen. Preferred halogens are chlorine, bromine and iodine, most preferably bromine.

Suzuki polymerization may be used to prepare homopolymers and regioregular, block and random copolymers ("copolymer" as used herein means a polymer comprising two or more different repeat units). In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

The repeat units of the polymer may be selected to tune the charge transporting and electroluminescent properties of the polymer. One widely used class of repeat units are amines, in particular triarylamines, as disclosed in, for example, WO 99/54385. Triarylamine repeat units may be used to provide both blue emission and hole transporting functionality, however the present inventors have found that polymerization of triarylamine-containing monomers can be quite slow.

Attaching aromatic groups to an aromatic repeat unit will typically result in extending the conjugation of the unit across the polymer, which in turn will shift the color of emission of the repeat unit towards shorter wavelengths (or, in other words, towards a smaller HOMO-LUMO bandgap). For example, U.S. Pat. No. 7,348,428 discloses polymers formed by polymerizing monomers having the formula:

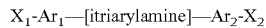

$X_1\text{-}Ar_1\text{—[itriarylamine]—}Ar_2\text{-}X_2$ wherein $X_1$ and $X_2$ are the same or different polymerizable groups, and wherein $Ar_1$ and $Ar_2$ are the same or different substituted or unsubstituted aryl or heteroaryl groups. U.S. Pat. No. 7,348,428 discloses in particular monomers wherein $Ar_1$ and $Ar_2$ are thiophene in order to obtain green emission, rather than blue emission, from the resulting polymer.

One object of the present invention is to provide polymers, in particular blue polymers, having a long half-life (that is, the time taken for the luminance of an emitter to halve at constant current). A further object of the invention is to provide polymers having high efficiency.

SUMMARY OF THE INVENTION

The skilled person will be aware that extending the number of aromatic groups in an aromatic repeat unit is expected to narrow the bandgap of that repeat unit. However, the present inventors have surprisingly found that aromatic groups can in fact be utilized to increase the bandgap of a repeat unit.

Furthermore, the present inventors have found that the inclusion of further aromatic groups in a monomer can increase the rate of reaction of that monomer, especially in the case of electron-rich monomers.

The present inventors have yet further found that inclusion of further aromatic groups in a monomer can lead to an increase in lifetime of the resultant polymer.

Accordingly, in a first aspect the invention provides a monomer.

In a particular embodiment, the monomer has formula (III):

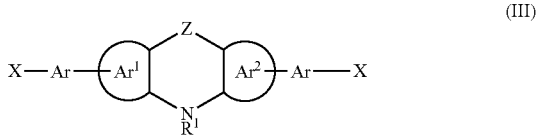

(III)

wherein X is a polymerisable group Ar, $Ar^1$ and $Ar^2$ each independently represent an optionally substituted aryl or heteroaryl group; $R^1$ represents H or a substituent; and Z represents a direct bond or a divalent linking atom or group.

Optionally, $Ar^1$ and $Ar^2$ are linked by a single bond or a divalent linking group selected from $CR^1R^2$, $SiR^1R^2$, $PR^1$, $NR^1$, O and S wherein $R^1$ and $R^2$ are independently selected from hydrogen; optionally substituted alkyl wherein one or more non-adjacent C atoms may be replaced with O, S, N, C=O and —COO—; alkoxy, aryl, arylalkyl, heteroaryl and heteroarylalkyl.

Optionally, $Ar^1$ and $Ar^2$ are linked by an oxygen atom.

Optionally, $Ar^1$ and/or $Ar^2$ may be fused to their respective adjacent Ar groups.

Optionally, $Ar^1$ and its adjacent Ar group and/or $Ar^2$ and its adjacent Ar group are fused to form a fluorene unit.

Optionally, X is a leaving group capable of participating in a metal insertion reaction.

Optionally, X is selected from the group consisting of boronic acid, boronic ester and halogen.

Optionally, Ar, $Ar^1$ and $Ar^2$ each independently represent a carbocyclic ring, preferably optionally substituted phenyl.

Optionally, one or both Ar groups are not in the same plane as the central part of the monomer. In particular, one or both Ar groups may be substituted, for example with a substituent $R^1$, thus creating a twist in the monomer. Preferably, the twist is at least 45 degrees.

In a second aspect, the invention provides a method of forming a polymer comprising the step of polymerizing a monomer according to the first aspect of the invention.

Optionally, the monomer is reacted with a comonomer to form a copolymer

Optionally, the polymer comprises fluorene repeat units and repeat units derived from the monomer of Formula (III).

Optionally, the polymerization takes place in the presence of a metal catalyst.

In a third aspect, the invention provides an organic electronic device, optionally an electroluminescent device, comprising a polymer according to the third aspect of the invention.

In a fourth aspect, the invention provides a method of forming a polymer comprising the step of polymerizing a monomer of formula (I):

wherein each Ar independently represents an optionally substituted aryl or heteroaryl group; Y represents a group comprising at least one aryl or heteroaryl group; p is 0 or an integer; q is at least 1; and X is a polymerisable group; and wherein the polymer has a peak photoluminescent wavelength that is longer than a corresponding polymer wherein p and q are both 0.

Optionally, the monomer is a monomer of formula (II):

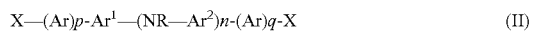

wherein $Ar^1$ and $Ar^2$ each independently represent an optionally substituted aryl or heteroaryl group; R is H or a substituent; and n is at least 1.

Optionally, —$Ar^1$—(NR—$Ar^2$)n- is selected from units 1, 2 and 3:

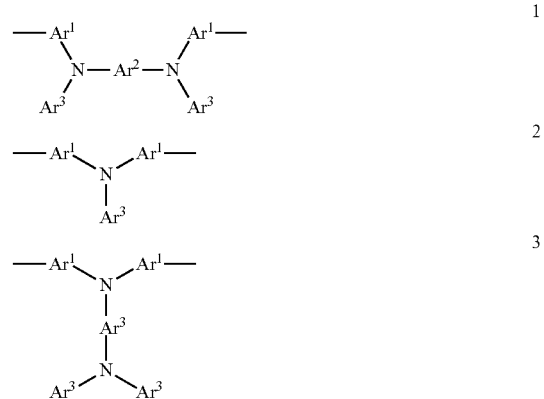

wherein $Ar^3$ is independently in each occurrence an optionally substituted aryl or heteroaryl group, and any of $Ar^1$, $Ar^2$ and $Ar^3$ may be linked to each other by a direct bond or a divalent linking atom or group.

Optionally, n=1

Optionally, $Ar^1$ and $Ar^2$ are linked by a single bond or a divalent linking group selected from $CR^1R^2$, $SiR^1R^2$, $PR^1$, $NR^1$, O and S wherein $R^1$ and $R^2$ are independently selected from hydrogen; optionally substituted alkyl wherein one or more non-adjacent C atoms may be replaced with O, S, N, C=O and —COO—; alkoxy, aryl, arylalkyl, heteroaryl and heteroarylalkyl.

Optionally, $Ar^1$ and $Ar^2$ are linked by an oxygen atom.

Optionally, $Ar^1$, and/or $Ar^2$ in the case where q is at least 1, may be fused to their respective adjacent Ar groups.

Optionally, $Ar^1$ and its adjacent Ar group and/or $Ar^2$ and its adjacent Ar group are fused to form a fluorene unit.

Optionally, adjacent Ar groups may be fused in the case where p and/or q is greater than 1.

Optionally, X is a leaving group capable of participating in a metal insertion reaction.

Optionally, X is selected from the group consisting of boronic acid, boronic ester and halogen.

Optionally, Ar, $Ar^1$ and $Ar^2$ each independently represent a carbocyclic ring, preferably optionally substituted phenyl.

Optionally, one or both Ar groups are not in the same plane as the central part of the monomer. In particular, one or both Ar groups may be substituted, for example with a substituent $R^1$, thus creating a twist in the monomer. Preferably, the twist is at least 45 degrees.

Optionally, q is at least 1.

Optionally, the polymer is a copolymer

Optionally, the polymer comprises fluorene repeat units and repeat units derived from the monomer of Formula (I).

Optionally, the polymerization takes place in the presence of a metal catalyst.

In a further aspect, the invention provides a polymer having a repeat unit:

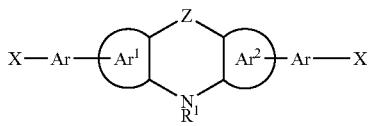

wherein Ar, $Ar^1$ and $Ar^2$ each independently represent an optionally substituted aryl or heteroaryl group; $R^1$ represents H or a substituent; and Z represents a direct bond or a divalent linking atom or group, wherein $Ar^1$ and $Ar^2$ are linked by a single bond or a divalent linking group selected from $CR^1R^2$, $SiR^1R^2$, $PR^1$, $NR^1$, O and S wherein $R^1$ and $R^2$ are independently selected from hydrogen; optionally substituted alkyl wherein one or more non-adjacent C atoms may be replaced with O, S, N, C=O and —COO—; alkoxy, aryl, arylalkyl, heteroaryl and heteroarylalkyl.

DETAILED DESCRIPTION OF THE INVENTION

Electron-rich monomers, for example monomers comprising at least one amine group, may beneficially be used to provide hole transport in a polymer. The repeat units derived from these monomers may also be used to provide emission. However, these monomers react more slowly in the polymerization reactions used to form semi-conducting polymers than electron-poor monomers. As used herein, an electron-rich monomer is a hydrocarbon monomer in which at least one carbon atom has been substituted by an atom or group with a greater quantity of unshared valence electrons than the carbon atom it has been substituted for. This results in different monomers being incorporated at different rates into the polymer, with electron-rich monomers being incorporated more slowly than electron-poor monomers. There is therefore a greater concentration of electron rich polymers towards the termini of the polymer.

Figure 1:
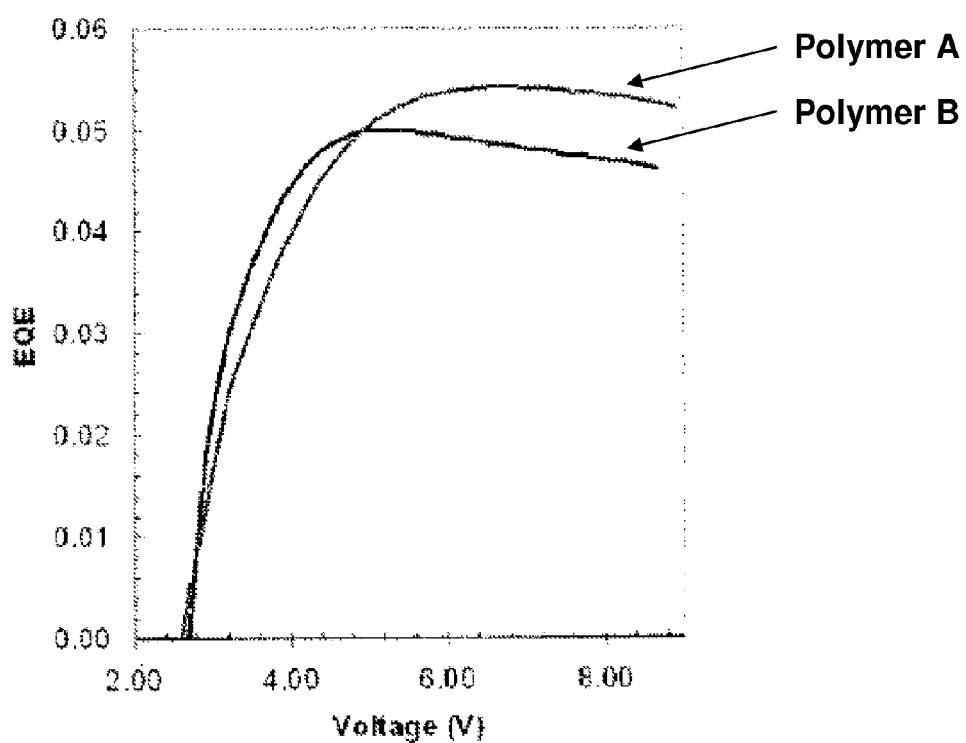
FIG. 1 shows the reduced efficiency of a low molecular weight polymer produced by using an excess of brominated monomer in a Suzuki polymerization.
Figure 2:
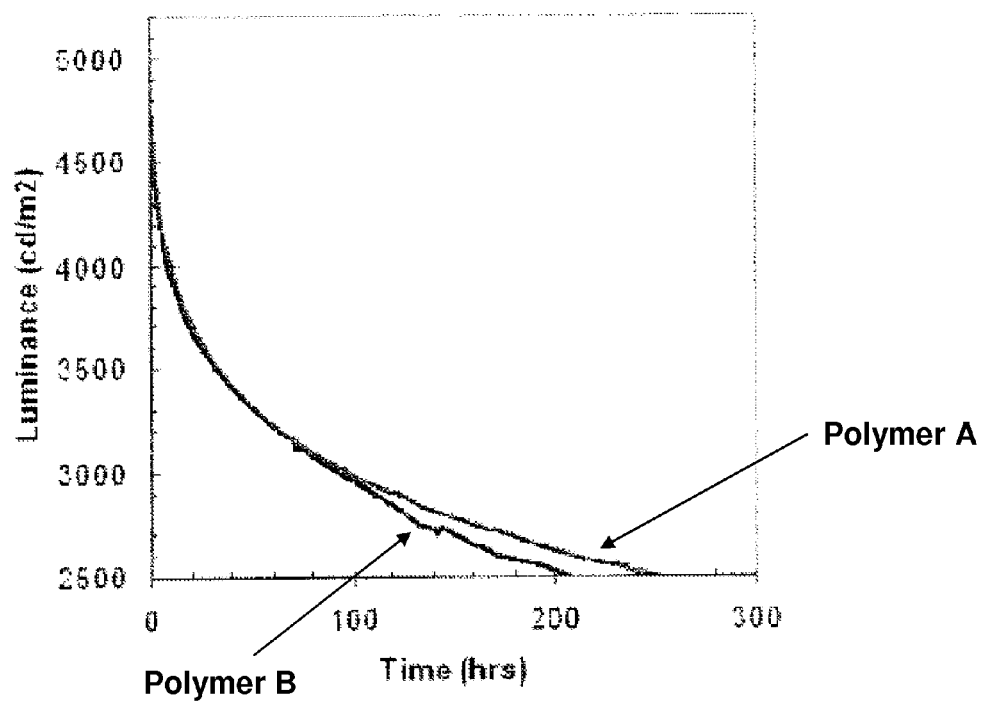
FIG. 2 shows the reduced lifetime of a low molecular weight polymer produced by using an excess of brominated monomer in a Suzuki polymerization.
Figure 3:
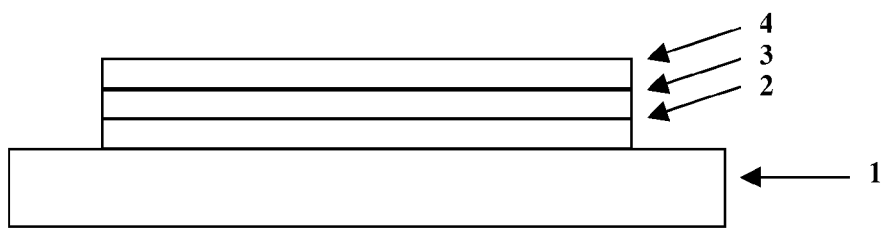
FIG. 3 provides an electroluminescent device according to the invention.

This effect is apparent if the molecular weight of the polymer is controlled (or at least partially controlled) by using an excess of brominated monomer in a Suzuki polymerization, as the relatively higher number of termini in a low molecular weight polymer (i.e. having a Mw of less than 250,000) leads to a greater proportion of electron-rich monomers being located towards the termini of the polymer. The resultant loss of efficiency and lifetime of the polymer is shown in FIGS. 1 and 2 respectively, in which A is a control polymer produced with a diester:dibromide ratio of 1:1, and B is a low molecular weight polymer produced with a diester:dibromide ratio of 0.98:1.

This uneven distribution of electron-rich groups is believed to be detrimental to both lifetime and efficiency of the material. It is believed that by providing Ar groups as described above in the monomer, the electron-rich groups are distributed more evenly, leading to a more even distribution of hole transporting units within the polymer chain.

The benefits provided by the present invention should also be obtained where electron-rich monomers will be incorporated towards the termini of the main chain or branches of the polymer for reasons other than rate of polymerization, for example where a greater percentage of electron rich monomers to electron poor monomers are used, or simply because of the chance involved in the polymerization reaction.

If one or both Ar groups of the monomer of the invention are twisted relative to one another, the bandgap of the repeat unit derived from that monomer will increase. In this way, the color of emission of the unit may be tuned. Alternatively, the monomer may be used to provide a charge-transporting unit along with a separate emissive unit, and in this case the degree of twisting of the Ar groups may be controlled to ensure that the repeat unit containing these Ar groups has a bandgap sufficiently high not to emit.

Polymers formed by the method of the present invention preferably comprise a repeat unit selected from arylene repeat units as disclosed in, for example, Adv. Mater. 2000 12(23) 1737-1750 and references therein. Exemplary first repeat units include: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

Particularly preferred polymers comprise optionally substituted, 2,7-linked fluorenes, most preferably repeat units of formula IV:

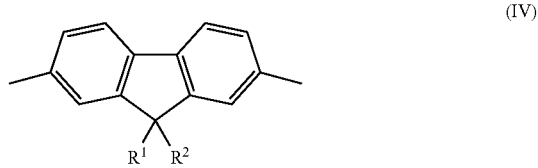

(IV)

wherein $R^1$ and $R^2$ are independently selected from hydrogen or optionally substituted alkyl wherein one or more non-adjacent C atoms may be replaced with O, S, N, C=O and —COO—, alkoxy, aryl, arylalkyl, heteroaryl and heteroarylalkyl. More preferably, at least one of $R^1$ and $R^2$ comprises an optionally substituted $C_4$-$C_{20}$ alkyl or aryl group.

In the case where R is aryl or heteroaryl, preferred optional substituents include alkyl groups wherein one or more non-adjacent C atoms may be replaced with O, S, N, C=O and —COO—.

Optional substituents for the fluorene unit, other than substituents $R^1$ and $R^2$, are preferably selected from the group consisting of alkyl wherein one or more non-adjacent C atoms may be replaced with O, S, N, C=O and —COO—, optionally substituted aryl, optionally substituted heteroaryl, alkoxy, alkylthio, fluorine, cyano and arylalkyl.

Preferably, the polymer comprises an arylene repeat unit as described above and an arylamine repeat unit, in particular a repeat unit V:

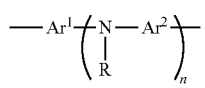
(V)

wherein Ar¹ and Ar² are optionally substituted aryl or heteroaryl groups, n is greater than or equal to 1, preferably 1 or 2, and R is H or a substituent, preferably a substituent. R is preferably alkyl or aryl or heteroaryl, most preferably aryl or heteroaryl. Any of the aryl or heteroaryl groups in the unit of formula 1 may be substituted. Preferred substituents include alkyl and alkoxy groups. Any of the aryl or heteroaryl groups in the repeat unit of Formula 1 may be linked by a direct bond or a divalent linking atom or group. Preferred divalent linking atoms and groups include O, S; substituted N; and substituted C.

Particularly preferred units satisfying Formula 1 include units of Formulae 1-3:

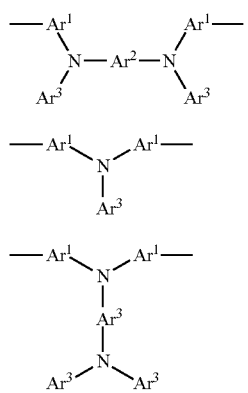

wherein Ar¹ and Ar² are as defined above; and Ar³ is optionally substituted aryl or heteroaryl. Where present, preferred substituents for Ar³ include alkyl and alkoxy groups.

Preferred concentration of the arylamine unit depends on the function of the polymer containing it. If the arylamine unit is present in a polymer for use in a hole transport layer it is preferably present in an amount up to 95 mol %, preferably up to 70 mol %. If the arylamine unit is present in a polymer for use in an emissive layer (as an emissive polymer or as the host for an emissive dopant) it is preferably present in an amount up to 30 mol %, preferably up to 20 mol %. These percentages apply to the total number of arylamine units present in the polymer in the case where more than one type of repeat unit of formula V is used.

The polymer may comprise heteroarylene repeat units for charge transport or emission. Preferred heteroarylene repeat units are selected from formulae 7-21:

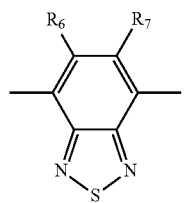
7 wherein $R_6$ and $R_7$ are the same or different and are each independently hydrogen or a substituent group, preferably alkyl, aryl, perfluoroalkyl, thioalkyl, cyano, alkoxy, heteroaryl, alkylaryl or arylalkyl. For ease of manufacture, $R_6$ and $R_7$ are preferably the same. More preferably, they are the same and are each a phenyl group.

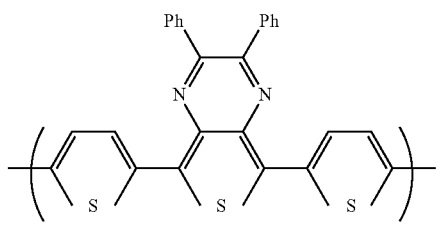
8

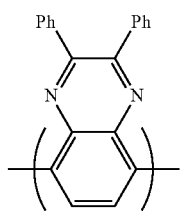
9

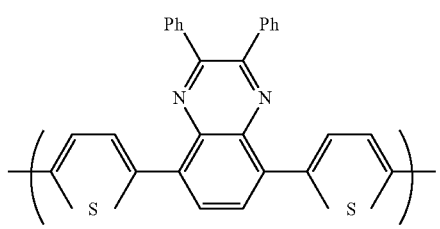
10

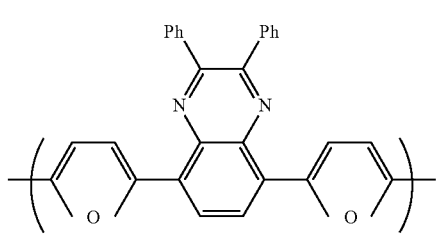
11

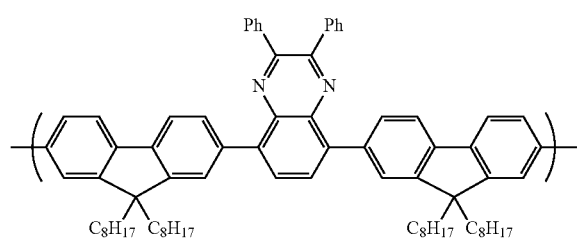
12

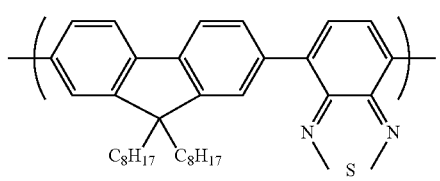
13

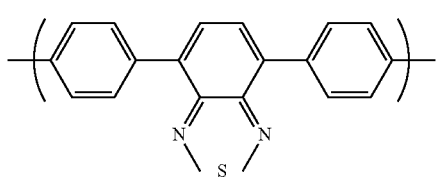

14

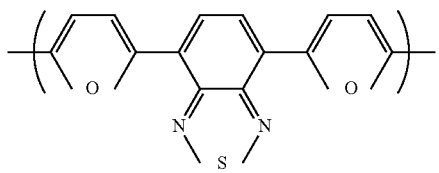

15

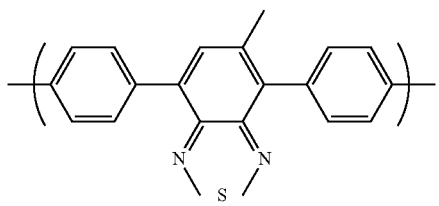

16

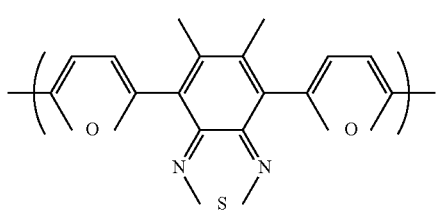

17

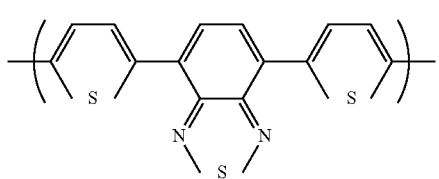

18

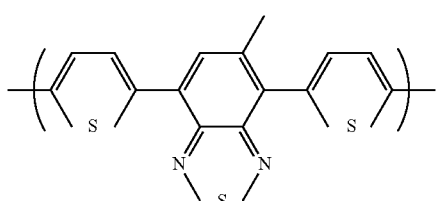

19

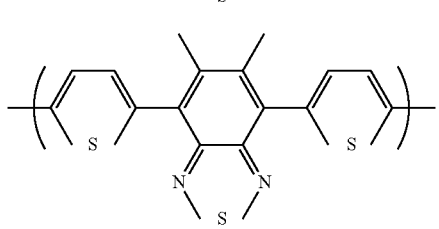

20

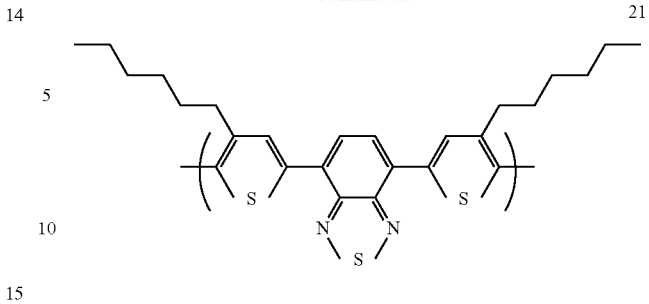

21

Electroluminescent copolymers may comprise an electroluminescent region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality. Alternatively, an electroluminescent polymer may be blended with a hole transporting material and/or an electron transporting material. Polymers comprising one or more of a hole transporting repeat unit, electron transporting repeat unit and emissive repeat unit may provide said units in a polymer main-chain or polymer side-chain.

The different regions within such a polymer may be provided along the polymer backbone, as per U.S. Pat. No. 6,353,083, or as groups pendant from the polymer backbone as per WO 01/62869.

Polymers formed by the method of the present invention may be used in an electroluminescent device to provide one or more of the functions of hole transport, electron transport and emission depending on which layer of the device it is used in and the nature of co-repeat units.

A polymer formed by the method of the present invention may also be used as a host material for an emissive dopant that may be mixed with or bound to the polymer. In this case, the polymer should have a higher excited state energy level than that of the dopant. In the case of a phosphorescent dopant, the $T_1$ energy level of the polymer should be sufficiently high for excited state energy to be transferred from the $T_1$ energy level of the host to the $T_1$ level of the emitter. Preferably, the host has a $T_1$ energy level sufficiently high to prevent energy back-transfer from the $T_1$ energy level of the emitter, and in particular a $T_1$ energy level higher than that of the emitter. However, in some cases the $T_1$ energy level of the host may be the same, or even lower, than that of the emitter.

Metal Complexes

Materials that may be used as fluorescent or phosphorescent dopants in the electroluminescent device include metal complexes comprising optionally substituted complexes of formula (VI):

$$ML^1_qL^2_rL^3_s \qquad (VI)$$

wherein M is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include:

lanthanide metals such as cerium, samarium, europium, terbium, dysprosium, thulium, erbium and neodymium; and d-block metals, in particular those in rows 2 and 3 i.e. elements 39 to 48 and 72 to 80, in particular ruthenium, rhodium, pallaidum, rhenium, osmium, iridium, platinum and gold.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission color is determined by the choice of the metal. The sharp emission is generally narrow, resulting in a pure color emission useful for display applications.

The d-block metals are particularly suitable for emission from triplet excited states. These metals form organometallic complexes with carbon or nitrogen donors such as porphyrin or bidentate ligands of formula (VII):

(VII)

wherein $Ar^4$ and $Ar^5$ may be the same or different and are independently selected from optionally substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred. Examples of bidentate ligands are illustrated below:

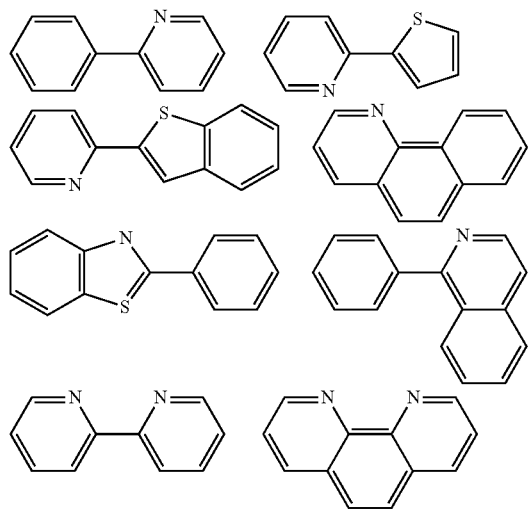

Each of $Ar^4$ and $Ar^5$ may carry one or more substituents. Two or more of these substituents may be linked to form a ring, for example an aromatic ring. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalize the ligand for attachment of further groups as disclosed in WO 02/68435 and EP 1245659; and dendrons which may be used to obtain or enhance solution processability of the metal complex as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the core and dendritic branches comprises an aryl or heteroaryl group.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission color is determined by the choice of ligand as well as the metal.

The host material and metal complex may be combined in the form of a physical blend. Alternatively, the metal complex may be chemically bound to the host material. In the case of a polymeric host, the metal complex may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

A wide range of fluorescent low molecular weight metal complexes are known and have been demonstrated in organic light emitting devices [see, e. g., Macromol. Sym. 125 (1997) 1-48, U.S. Pat. Nos. 5,150,006, 6,083,634 and U.S. Pat. No. 5,432,014]. Suitable ligands for di or trivalent metals include: oxinoids, e. g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), schiff bases, azoindoles, chromone derivatives, 3-hydroxyflavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission color.

With reference to FIG. 4, the architecture of an electroluminescent device according to the invention comprises a transparent glass or plastic substrate 1, an anode 2 and a cathode 4. An electroluminescent layer 3 is provided between anode 2 and cathode 4.

In a practical device, at least one of the electrodes is semi-transparent in order that light may be emitted. Where the anode is transparent, it typically comprises indium tin oxide.

Further layers may be located between anode 2 and cathode 3, such as charge transporting, charge injecting or charge blocking layers.

Polymerization method

The method of the invention may entail a metal-catalyzed polymerization reaction which operates via a metal insertion wherein the metal atom of a metal complex catalyst is inserted between an aryl group and a leaving group of a monomer, in particular Suzuki polymerization as described in, for example, WO 00/53656 and Yamamoto polymerization as described in, for example, T. Yamamoto, "Electrically Conducting And Thermally Stable π - Conjugated Poly(arylene)s Prepared by Organometallic Processes", Progress in Polymer Science 1993, 17, 1153-1205.

In the case of Yamamoto polymerization, a nickel complex catalyst is used and the monomer comprises at least two reactive halogen groups. In the case of Suzuki polymerization, a palladium complex catalyst is used in the presence of a base; at least one reactive group is a boron derivative group such as a boronic acid or boronic ester; and the other reactive group is a halogen.

Pereferred halogens are chlorine, bromine and iodine, most preferably bromine. Other reactive leaving groups that may be used in place of halogen include esters of sulfonic acids such as mesiylate and triflate groups.

The polymers are preferably end-capped. An end-capping reagent may be added at the end of the polymerization. However, in some cases it may be beneficial to add the end-capping reagent during or at the start of polymerization, for example in order to control the polymer's molecular weight.

By providing a polymerization mixture wherein the different monomers have approximately the same reactivity, the distribution of repeat units along the polymer chain is more even than in comparison to a mixture where the monomers have different reactivities. In order to further control distribution of repeat units, block polymerization techniques may be used wherein different monomers are added at different times during the polymerization reaction.

Charge Injection Layers

It is particularly desirable to provide a conductive hole injection layer, which may be formed from a conductive organic or inorganic material provided between the anode 2 and the electroluminescent layer 3 to assist hole injection from the anode into the layer or layers of semiconducting polymer. Examples of doped organic hole injection materials include doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Electroluminescent and Charge Transporting Layers

If present, a hole transporting layer located between anode 2 and electroluminescent layer 3 preferably has a HOMO level of less than or equal to 5.5 eV, more preferably around 4.8-5.5 eV. HOMO levels may be measured by cyclic voltammetry, for example.

If present, an electron transporting layer located between electroluminescent layer 3 and cathode 4 preferably has a LUMO level of around 3-3.5 eV.

Electroluminescent layer 3 may consist of the electroluminescent material alone or may comprise the electroluminescent material in combination with one or more further materials. In particular, the electroluminescent material may be blended with hole and/or electron transporting materials as disclosed in, for example, WO 99/48160, or may comprise a luminescent dopant in a semiconducting host matrix. Alternatively, the electroluminescent material may be covalently bound to a charge transporting material and/or host material.

Electroluminescent layer 3 may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

Suitable materials for use in layer 3 include small molecule, polymeric and dendrimeric materials, and compositions thereof. Suitable electroluminescent polymers for use in layer 3 include poly(arylene vinylenes) such as poly(p-phenylene vinylenes) and polyarylenes such as: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. Such polymers as disclosed in, for example, Adv. Mater. 2000 12(23) 1737-1750 and references therein. Suitable electroluminescent dendrimers for use in layer 3 include electroluminescent metal complexes bearing dendrimeric groups as disclosed in, for example, WO 02/066552.

Cathode

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminum. Alternatively, it may comprise a plurality of metals, for example a bilayer of a low workfunction material and a high workfunction material such as calcium and aluminum as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode will comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminum. Examples of transparent cathode devices are disclosed in, for example, GB 2348316.

Encapsulation

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A getter material for absorption of any atmospheric moisture and/or oxygen that may permeate through the substrate or encapsulant may be disposed between the substrate and the encapsulant.

The embodiment of FIG. 4 illustrates a device wherein the device is formed by firstly forming an anode on a substrate followed by deposition of an electroluminescent layer and a cathode, however it will be appreciated that the device of the invention could also be formed by firstly forming a cathode on a substrate followed by deposition of an electroluminescent layer and an anode.

Solution Processing

A single polymer or a plurality of polymers may be deposited from solution to form layer 3. Suitable solvents for polyarylenes, in particular polyfluorenes, include mono- or poly-alkylbenzenes such as toluene and xylene. Particularly preferred solution deposition techniques including printing and coating techniques, preferably spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full color displays. A device may be inkjet printed by providing a patterned layer over the first electrode and defining wells for printing of one color (in the case of a monochrome device) or multiple colors (in the case of a multicolor, in particular full color device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

EXAMPLES

Example 1

A monomer was prepared as per the following scheme.

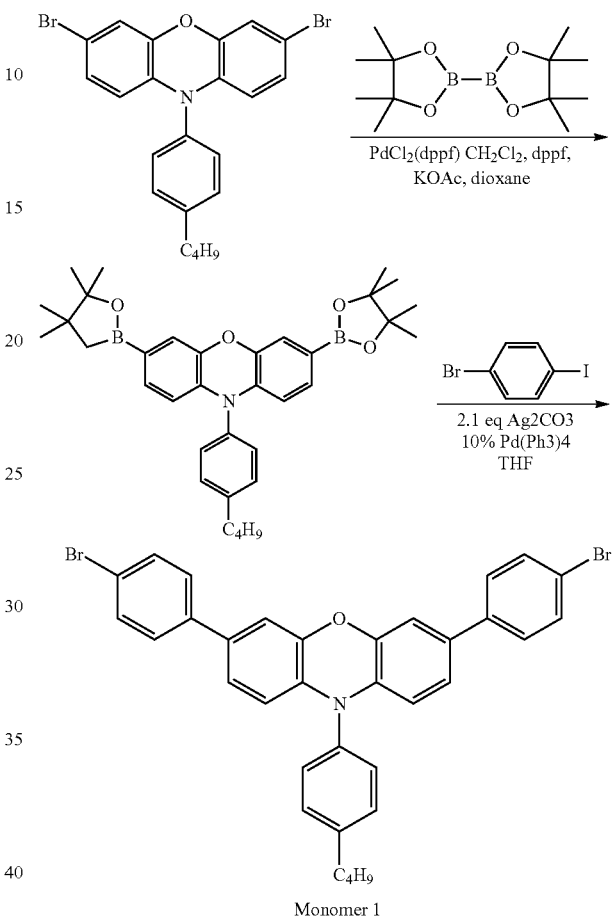

Monomer 1

Monomer 1 underwent Suzuki polymerization with an ester of 2,7-diboronic acid-9,9-dioctylfluorene Comparative Example 1

A polymer was prepared as per Example 1 with the exception that the following monomer was used in place of Monomer 1:

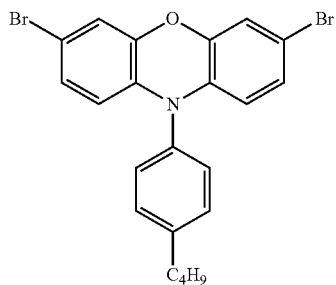

The polymer was found to comprise amine groups at the polymer chain ends. Without wishing to be bound by any theory, it is believed that the electron-rich nature of amine-based monomers tends to reduce their reactivity as compared to the other, more electron-deficient monomers used in the polymerization. This results in amine groups at the polymer chain ends, which in turn leads to an uneven distribution of charge transporting amine groups within the polymer chain.

However, the present inventors have found that the reactivity of the monomer may be increased by providing at least one Ar group between the amine and the reactive leaving group, such that the reactivity of the monomer is similar to the reactivity of the other monomers used in the reaction. In this way, the repeat units along the polymer backbone are more evenly distributed which in turn leads to increased efficiency and lifetime of the polymer.

In addition to increasing reactivity, the Ar groups serve as "spacers" to separate amine units from one another in the polymer chain which again has the effect of providing for more even distribution of amine units within the polymer backbone.

Furthermore, in the case where the amine is the emissive unit of an electroluminescent polymer, the color of emission of the polymer may be tuned by appropriate selection of Ar groups. This can be seen from the table below, which illustrates the effect of various Ar groups on bandgap (Eg) of the repeat unit.

| Structure | Number of monomers n | 1/n | HOMO | LUMO | Eg | EC bandgap (HOMO-LUMO) |
|---|---|---|---|---|---|---|
| 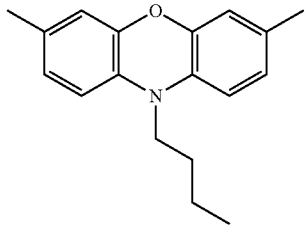 | 1<br>3<br>5 | 1<br>0.33333<br>0.2 | −7.0617 | −0.3082 | 3.654 | <br><br>6.7535 |
| 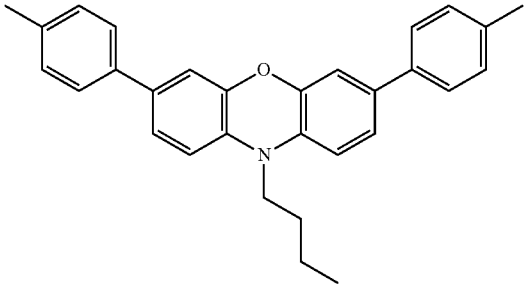 | 1<br>3<br>5 | 1<br>0.33333<br>0.2 | −7.1166 | −0.3366 | | 0<br><br>6.78 |
| 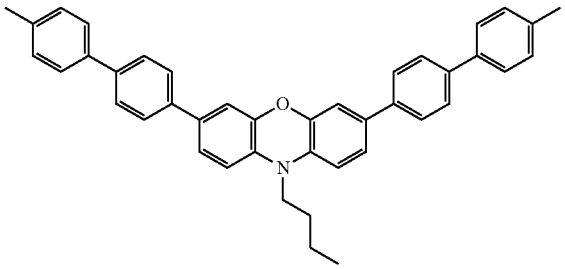 | 1<br>3<br>5 | 1<br>0.33333<br>0.2 | −7.1327 | −0.355 | | 0<br>0<br>6.7777 |
| 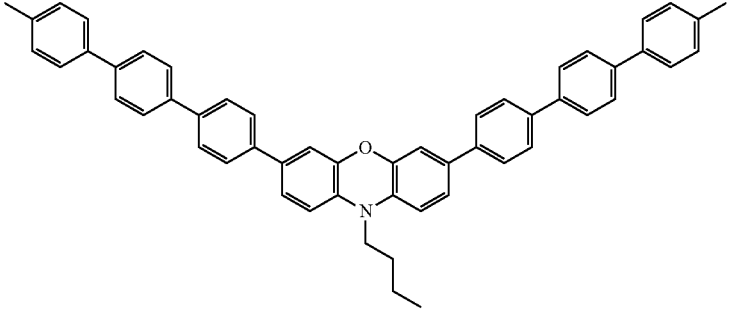 | 1<br>3<br>5 | 1<br>0.33333<br>0.2 | −7.1469 | −0.3689 | | 0<br>0<br>6.7771 |

The invention claimed is:

1. A method of forming a polymer comprising polymerizing a monomer of formula (III):

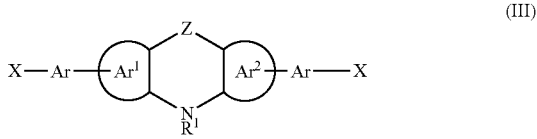

wherein X is a polymerizable group Ar, $Ar^1$ and $Ar^2$ each independently represent an optionally substituted aryl or heteroaryl group; $R^1$ represents H or a substituent; and Z represents a direct bond or a divalent linking atom or group, wherein $Ar^1$ and $Ar^2$ are linked by a single bond or a divalent linking group selected from $CR^1R^2$, $SiR^1R^2$, $PR^1$, $NR^1$, O and S wherein $R^1$ and $R^2$ are independently selected from hydrogen; optionally substituted alkyl wherein one or more non-adjacent C atoms may be replaced with O, S, N, C=O and —COO—; alkoxy, aryl, arylalkyl, heteroaryl and heteroarylalkyl.

2. A method according to claim 1 comprising reacting the monomer with a comonomer to form a copolymer.

3. A method according to claim 2 wherein the polymer comprises fluorene repeat units and repeat units derived from the monomer of Formula (III).

4. A method according to claim 1 wherein the polymerization takes place in the presence of a metal catalyst.

5. A method according to claim 1 wherein $Ar^1$ and $Ar^2$ are linked by an oxygen atom.

6. A method according to claim 1 wherein $Ar^1$ and / or $Ar^2$ are bonded to their respective adjacent Ar groups by a carbon to carbon bond.

7. A method according to claim 1 wherein $Ar^1$ and / or $Ar^2$ are fused to their respective adjacent Ar groups.

8. A method according to claim 7 wherein $Ar^1$ and its adjacent Ar group and / or $Ar^2$ and its adjacent Ar group are fused to form a fluorene unit.

9. A method according to claim 1 wherein X is a leaving group capable of participating in a metal insertion reaction.

10. A method according to claim 9 wherein X is selected from the group consisting of boronic acid, boronic ester and halogen.

11. A method according to claim 1 wherein Ar, $Ar^1$ and $Ar^2$ each independently represent a carbocyclic ring.

12. A method according to claim 11 wherein the carbocyclic ring is optionally substituted phenyl.

* * * * *